(12) United States Patent
Hepburn et al.

(10) Patent No.: US 6,908,475 B2
(45) Date of Patent: Jun. 21, 2005

(54) DEVICE FOR TREATING CARPAL TUNNEL SYNDROME

(75) Inventors: George R. Hepburn, Severna Park, MD (US); Russell Vedeloff, Greensboro, MD (US); Terry A. Meharry, Tuscaloosa, AL (US)

(73) Assignee: Dynasplint Systems, Inc., Severna Park, MD (US)

( * ) Notice: Subject to any disclaimer, the term of this patent is extended or adjusted under 35 U.S.C. 154(b) by 0 days.

(21) Appl. No.: 10/159,614

(22) Filed: May 30, 2002

(65) Prior Publication Data

US 2003/0225349 A1 Dec. 4, 2003

(51) Int. Cl.[7] .......................... A61B 17/54; A61B 17/62; A61B 17/66
(52) U.S. Cl. .......................... 606/201; 606/204; 601/40; 601/133; 601/134; 602/21
(58) Field of Search ................................ 606/201, 204; 601/40, 134, 133, 135; 602/21

(56) References Cited

U.S. PATENT DOCUMENTS

| | | | | |
|---|---|---|---|---|
| 285,160 A | * | 9/1883 | Rice | 601/133 |
| 2,664,884 A | * | 1/1954 | La Verne | 601/135 |
| 3,837,336 A | * | 9/1974 | Taubert | 601/133 |
| 4,249,534 A | * | 2/1981 | Muldrow, Jr. | 606/201 |
| 4,557,262 A | * | 12/1985 | Snow | 606/201 |
| 5,094,227 A | * | 3/1992 | Eglauf et al. | 601/135 |
| 5,366,436 A | | 11/1994 | Gibney | 601/40 |
| 5,468,220 A | * | 11/1995 | Sucher | 606/201 |
| 5,492,525 A | | 2/1996 | Gibney | 601/40 |
| 5,514,052 A | | 5/1996 | Charles et al. | 482/47 |
| 5,551,933 A | | 9/1996 | Washburn | 482/44 |
| 5,584,854 A | * | 12/1996 | Minarik | 606/201 |
| 5,613,923 A | | 3/1997 | Anliker | 482/48 |
| 5,709,647 A | * | 1/1998 | Ferber | 601/134 |
| 5,728,120 A | * | 3/1998 | Shani et al. | 606/201 |
| 5,769,758 A | * | 6/1998 | Sarkinen | 482/44 |
| 6,010,431 A | | 1/2000 | Taylor | 482/44 |
| 2002/0151930 A1 | * | 10/2002 | Mills | 606/204 |
| 2003/0130690 A1 | * | 7/2003 | Porrata et al. | |

FOREIGN PATENT DOCUMENTS

JP            2001000504 A   *  1/2001

* cited by examiner

*Primary Examiner*—Danton DeMille
(74) *Attorney, Agent, or Firm*—Armstrong, Kratz, Quintos, Hanson & Brooks, LLP

(57) ABSTRACT

A therapeutic device for applying graded compression to the hand to remedy the symptoms of carpal tunnel syndrome. The device is a passive therapy device which receives the palm of the hand and applies graduated pressure to the top of the hand to relieve carpal tunnel region of the hand by spreading the area of the carpal tunnel.

9 Claims, 19 Drawing Sheets

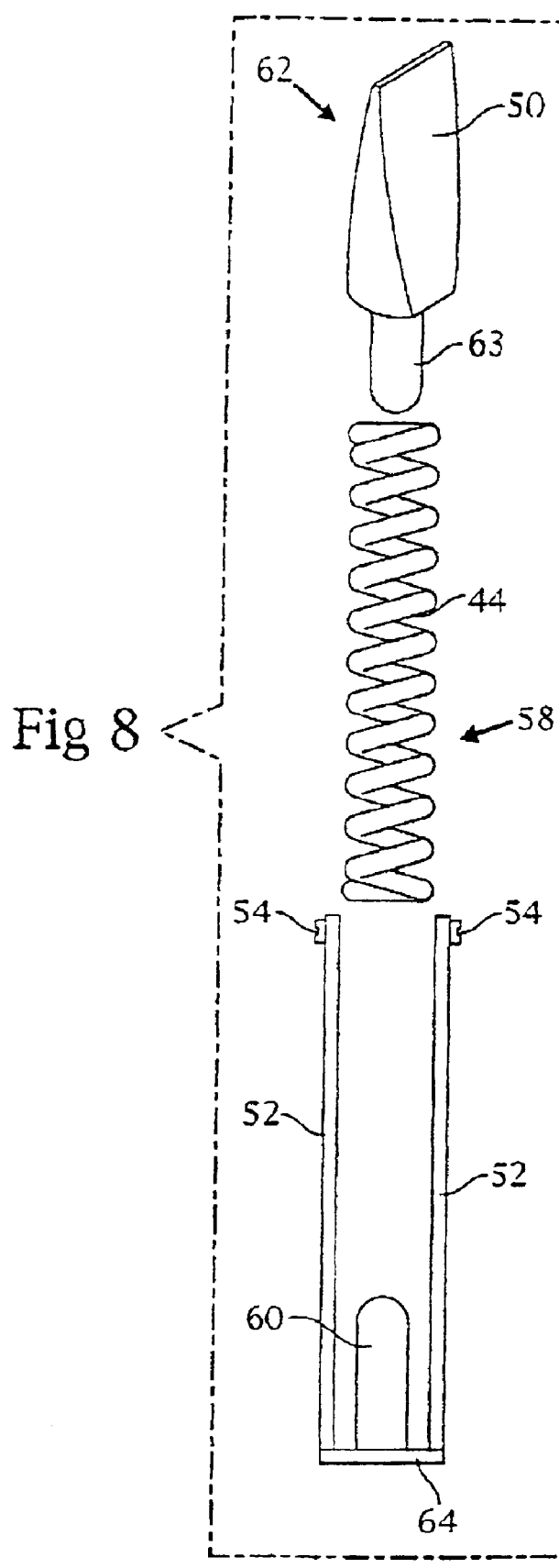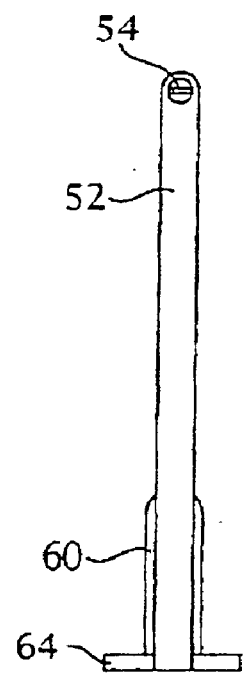

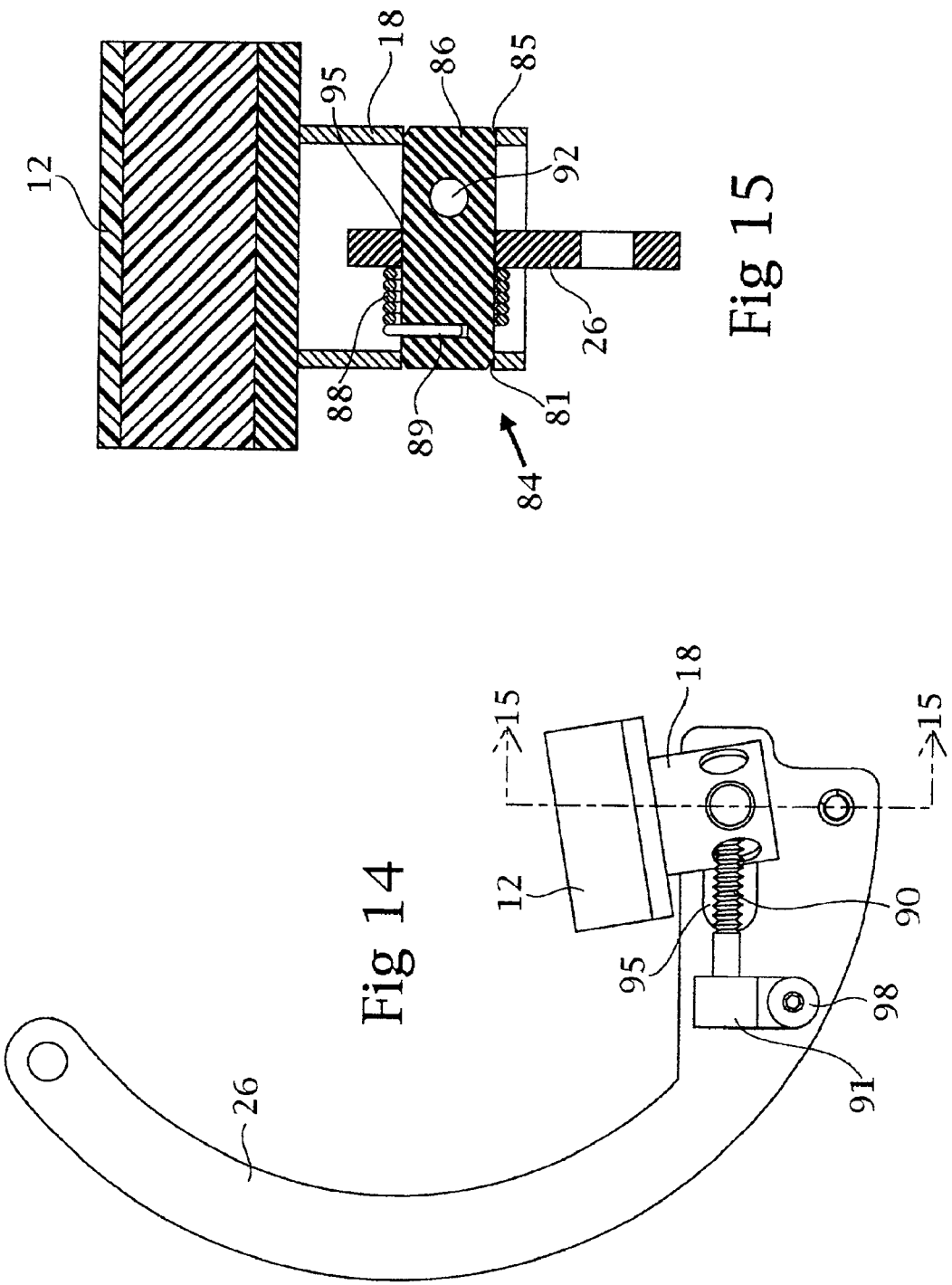

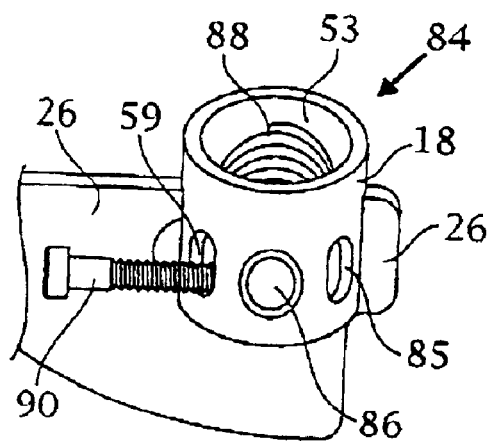
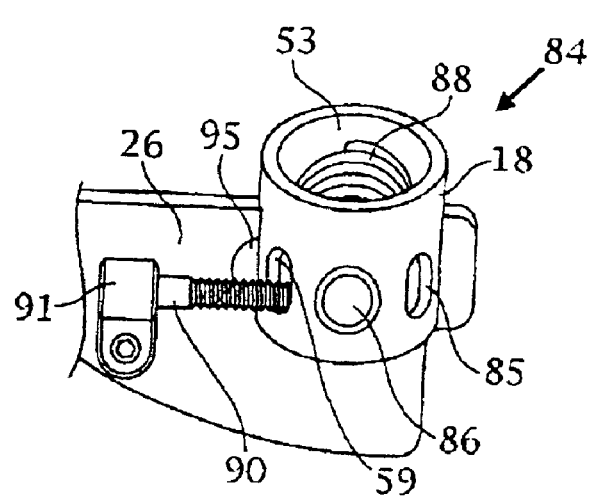
Fig 20　　　　　　　　　Fig 21
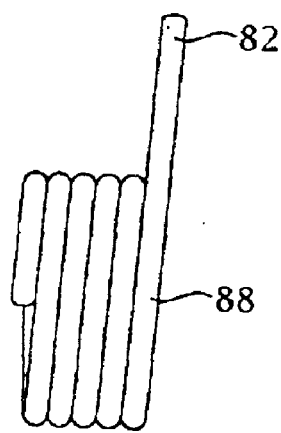
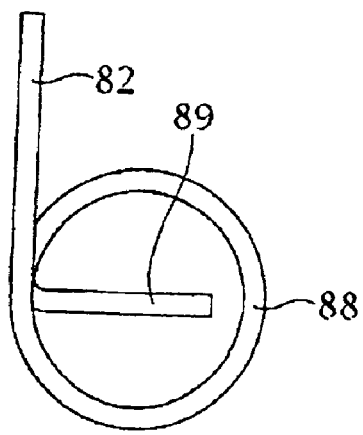
Fig 22　　　　　　　　　Fig 23

DEVICE FOR TREATING CARPAL TUNNEL SYNDROME

FIELD OF THE INVENTION

The herein disclosed invention finds applicability in the field of therapeutic devices used to free-up stiff muscles and stiff joints. In particular, the invention is directed to relieving the effects of carpal tunnel syndrome.

BACKGROUND OF THE INVENTION

A moderately active individual makes thousands of different hand movements in a single day. Such activity may lead to repetitive strain injuries, such as carpal tunnel syndrome (CTS), in which the tendons and ligaments in the carpal tunnel swell and compress nerves, resulting in hand numbness.

The increase of computer keyboards in offices and homes has created a dramatic increase in the number of repetitive strain injuries such as carpal tunnel syndrome. Carpal tunnel syndrome (CTS) is believed to be caused by compression of the median nerve resulting from a swelling of tendons and sheaths. Swelling of the tendons in the carpal tunnel reduces circulation to the hands causing numbness and pain. It is well known that a person who performs repetitive motions with his hands might develop a repetitive stress injury such as carpal tunnel syndrome.

Individuals who spend extended periods of time with their wrist in a flexed condition may develop CTS. A major cause of CTS is the continuous flexing of the wrist which is particularly common amongst individuals who spend long periods of time at keyboards, whether such keyboards be associated with computers per se, or with cash registers or other such devices. Such flexing is generally accompanied by pronation of the hand, i.e., holding the palm in a downward facing position, which further strains the connective tissue and nerves running through the carpal tunnel. Musicians are also subject to CTS, CTS itself is caused by compression of the median nerve, which runs through the wrist and branches into the palm, thumb and first three fingers. The median nerve runs through a bony structure which is identified as the carpal tunnel. The flexor tendons and the carpal ligament in the carpal tunnel may swell due to repetitive hand movements, pinching the medial nerve and producing the condition known as CTS. CTS generally results in an inability effectively to grip with the hands, and is usually accompanied by a tingling and numbness in the fingers.

The herein disclosed invention is designed to provide a therapy device for relieving the effect of carpal tunnel syndrome; and to bring flexibility to the hand and wrist as soon as possible.

BRIEF SUMMARY OF THE INVENTION

The Dynasplint™ carpal tunnel therapy device of this invention is a mechanical device for applying pressure at three points by means of a graded tensioning mechanism to create an "opening" or spread of the carpal tunnel, thereby, relieving stress and compression of the median nerve. Pressure is applied for relatively prolonged periods of time with a graded increase of pressure to allow for the relief of pressure on the median nerve which is being impinged, producing symptoms associated with carpal tunnel syndrome. The carpal tunnel therapy device is unique in being able to adjust for the degree of tension to be applied to the hand to relieve pressure on the nerve.

The Dynasplint Carpal Tunnel Syndrome (CTS) System is designed to treat, a disorder marked by compression of the carpal tunnel region in the wrist. CTS is a disabling wrist/hand condition usually involving tightening of the transverse carpal ligament causing compression of the median nerve, artery and vein. Signs and symptoms of numbness, tingling, burning and muscle weakness can occur.

CTS can be very disabling often resulting in partial loss of the use of the hand. Treatment frequently consists of surgical release of the transverse carpal ligament with weeks of recovery needed. Often times physical therapy is employed both pre- and post operatively.

The success rate for treatment of CTS has varied greatly. Even with surgery, many patients are left with continued weakness and/or paresthesias. Occupations involving hand use, ranging anywhere from secretarial duties such as typing and writing to the carpenter's need to use a screwdriver can cause CTS and be difficult for the patient to resume normal activity once this disabling condition develops. CTS has an etiology associated with repetitive trauma syndrome (RTS), which occurs when relatively minor traumas occur many times over a period of weeks or months. The cumulative stress then causes the tissue around the carpal tunnel to shrink and tighten (forming a contracture) which in turn compresses the enveloped tissues (median nerve, vein and artery). This compression then "cuts off" the vitally important nerve conductivity and blood flow which in turn results in the disabling muscle weakness of the thumb, index and middle fingers and causes paresthesias of the same digits plus the radial side of the $4^{th}$ digit.

The purpose of the Dynasplint CTS system is to restore the normal length of the transverse carpal ligament and other associated surrounding tissues so that the median nerve, vein and artery have less compression which then allows freer blood flow and improved nerve conductivity. This compressive relief can then lead to abatement of paresthesias, improved muscle strength and overall improved hand function thereby allowing return to work and other activities.

The CTS System is designed to be used for 30–60-minute sessions, 1–3 times per day with low tension progressing as tolerated to higher levels of tension. Total duration of wear may be up to three months or longer but frequently less time of wear will be curative.

Prior Art Patents

Taylor (U.S. Pat. No. 6,010,431) teaches an exercise device for relieving carpal tunnel syndrome by pushing down of the hand to urge apart opposite sides of the palm to thereby relieve compression on the blood vessels and nerves.

Anliker (U.S. Pat. No. 5,613,923) teaches a device for treating repetitive strain injury which employs a glove, a resilient member and an anchor mechanism, wherein the user's fingers and thumb are extended. In actual use the user's fingers and wrist are extended; and the user's fingers and thumb are abducted. The user encounters resistance, exercising the extensor muscles of the fingers, hand, wrist and elbow, thereby relieving carpal tunnel syndrome.

Washburn (U.S. Pat. No. 5,551,933) teaches a hand-held device with a bead on a series of loops serving as a track for the bead. The bead is moved along the track by wrist-motion. This wrist motion exercises the wrist, thereby relieving carpal tunnel syndrome.

Gibney (U.S. Pat. No. 5,492,525) and (U.S. Pat. No. 5,366,436) teaches an exercise device to treating symptoms related to carpal tunnel syndrome. The thumb fingers are inserted into the device; and the thumb and fingers are stretched away from each other. This exercise is designed to relieve carpal tunnel syndrome.

Charles (U.S. Pat. No. 5,514,052) teaches a finger exerciser to relieve carpal tunnel syndrome. The device can retain the fingers and can apply tension to the fingers by means of tension stays which apply tension to elastic cords. By stretching the fingers and strengthening extensor muscles of the wrist, hand and fingers, the ill-effects of carpal tunnel syndrome are alleviated.

None of the prior art cited shows a graded tensioning mechanical device such as described by this invention for treating carpal tunnel syndrome.

OBJECTS OF THE INVENTION

A main object of the invention is to efficiently treat carpal tunnel syndrome.

A further object of this invention is to produce a therapy device which will allow for rapid rehabilitation of stiff fingers and hand.

Another object of this invention is to produce a device with a tension mechanism which is adjustable to produce greater or lesser tension-pressure or force on the hand as required.

Other objects of the present invention will become apparent from a reading of the following specification taken in conjunction with the enclosed drawings.

These and other objects of the present invention will become apparent from a reading of the following specification taken in conjunction with the enclosed drawings.

BRIEF DESCRIPTION OF THE DRAWINGS

FIG. 8 is a view of the chisel tip and indicator gauge assembly of the tensioning mechanism used in the carpal tunnel syndrome therapy device.

FIG. 9 is a view of indicator gauge assembly of the device shown in FIG. 8 turned 90°.

FIG. 14 is a front plan view of the left side foot yoke and bracket.

FIG. 15 is a sectional view of the foot yoke taken along 15—15 of FIG. 14.

FIGS. 16–21 are views illustrating the components of the foot yoke and the order for assembling and placement on the bracket.

FIGS. 22 and 23 are a side plan view and an end view of the torsion spring used in the foot yoke assembly.

DESCRIPTION

Figure 1:
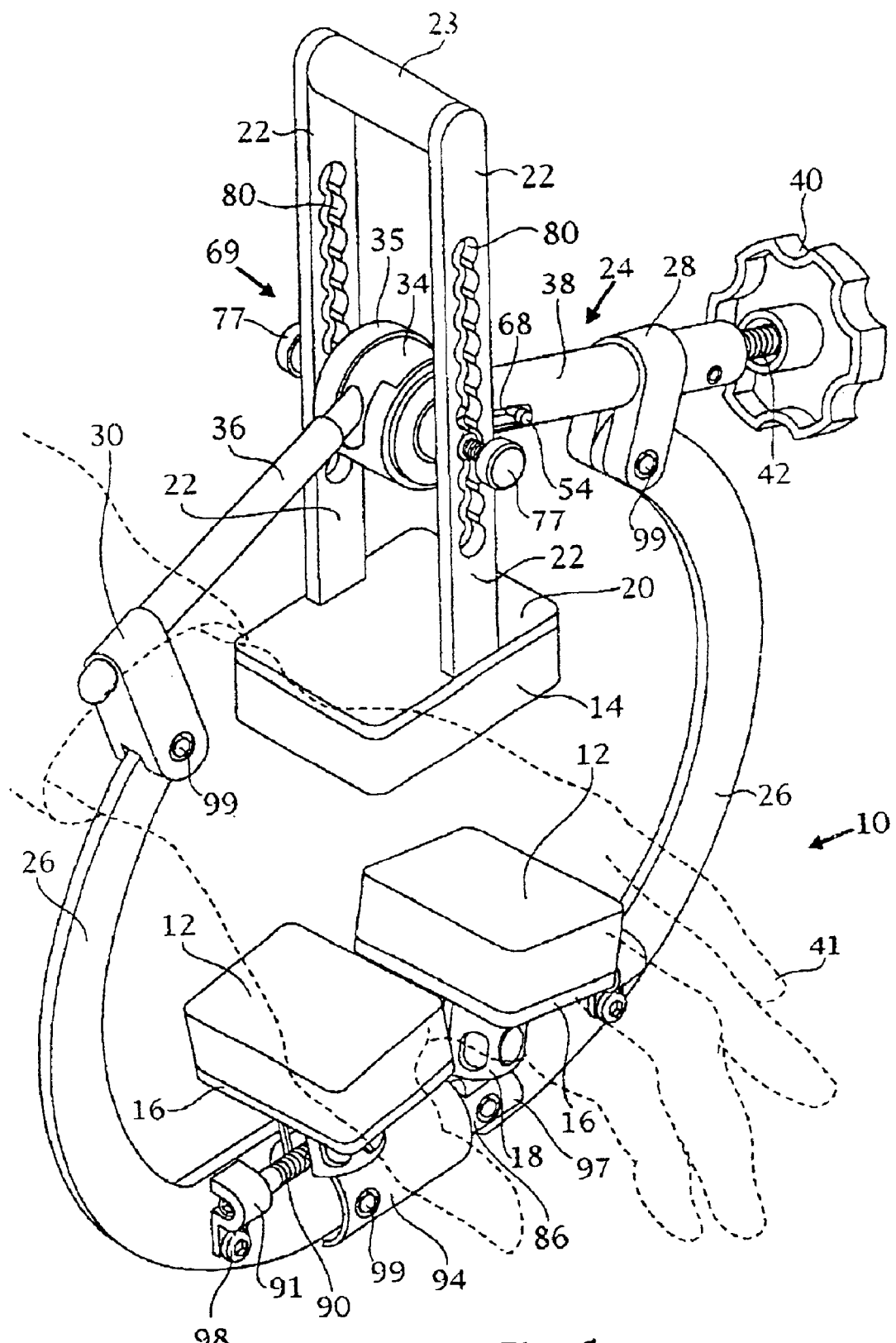
FIG. 1 is a perspective view of the carpal tunnel syndrome therapy device.
Figure 2:
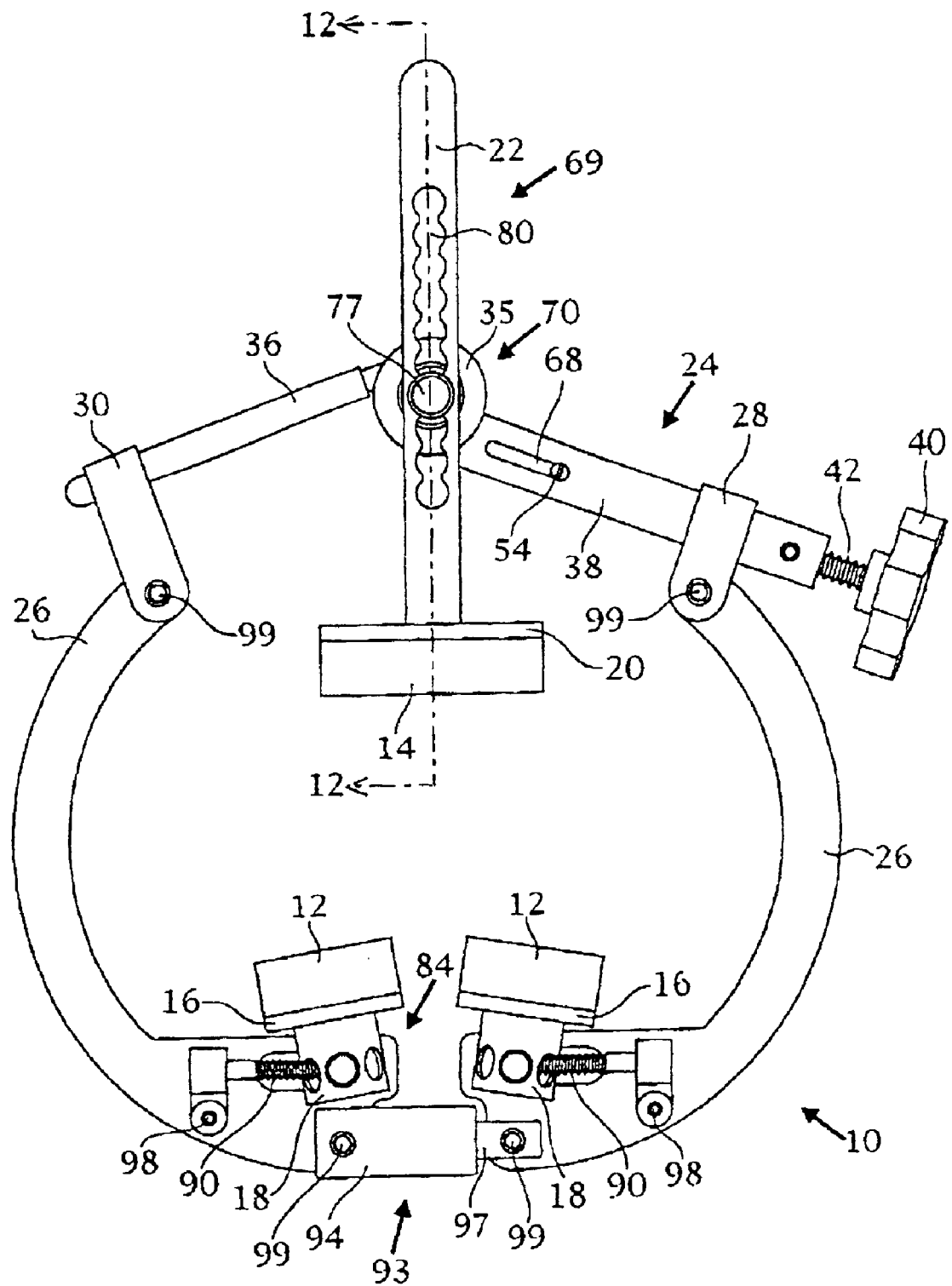
FIG. 2 is a front plan view thereof.
Figure 3:
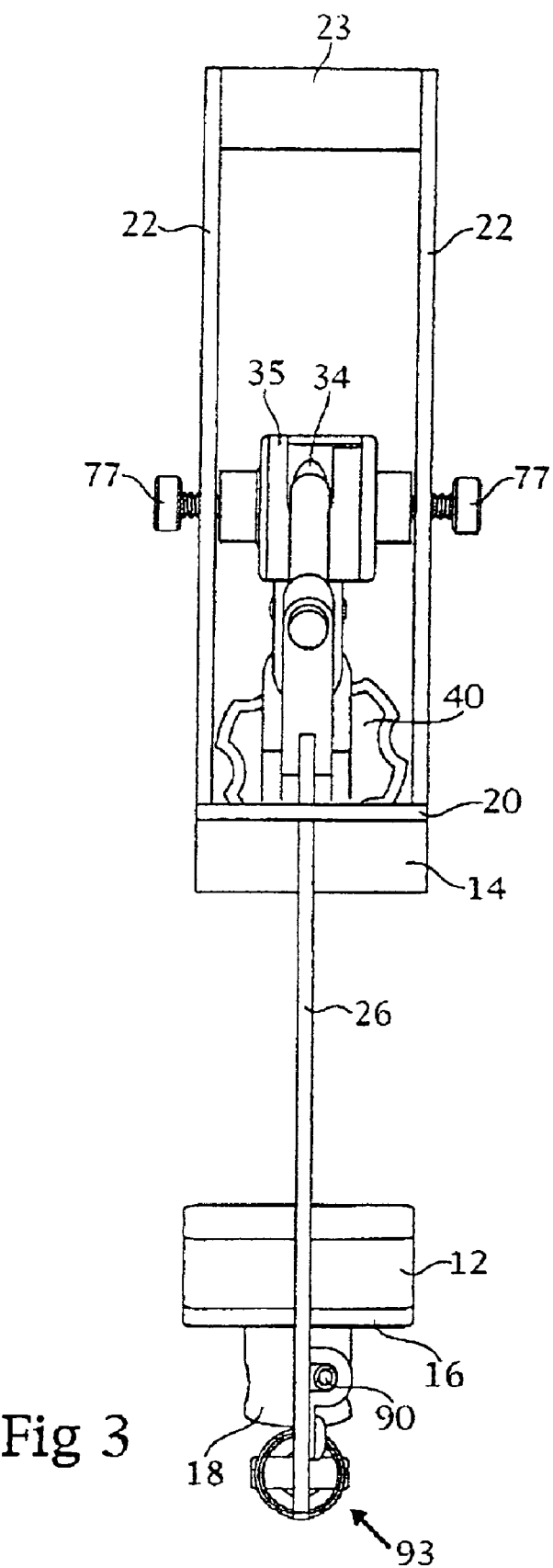
FIG. 3 is a left side elevational view thereof.

With reference to FIGS. 1 to 3 a carpal tunnel syndrome therapy device 10 is provided with carpal pads 12 and a counter force pad 14. The carpal pads 12 are supported on a pair of carpal foots 16 which in turn are attached to a pair of carpal foot yokes 18. The counter force pad is attached to a counter force foot 20 which in turn is attached to a pair of counter force brackets 22. The counter force brackets 22 are joined at the top by a bracket bar 23 and joined at the bottom by a counter force foot 20.

The carpal tunnel therapy device is provided with a drive assembly 24 (shown in detail in FIGS. 4–11) which is attached to a pair of carpal tunnel brackets 26, by way of housing tube yoke 28 and stem rod yoke 30 (FIGS. 1 and 2). As best shown in FIGS. 4–12, there is a drive assembly having a stem rod 36 attached to a main joint 34 which is inserted into a housing tube head 35 attached to a housing tube 38 and at the end of the housing tube there is disposed a loading screw knob 40 attached to loading screw 42.

FIGS. 4–7 are views of the drive assembly 24. The tension mechanism is contained in a housing tube 38 and has a loading screw knob 40 and loading screw 42 which presses an indicator bar 52 and spring spacer 60 as best shown in FIGS. 8 and 9. With particular reference to FIGS. 8 and 9, the compression spring 44 fits over the spring spacer 60 onto bottom support 64 of the spring spacer 60 and chisel tip 50 fits inside and over the compression spring 44. In turn, the chisel tip 50 abuts the keeper 37 of the main joint 34 joined to stem rod 36. Main joint 34 assembly is housed in housing head 35.

Figure 6:
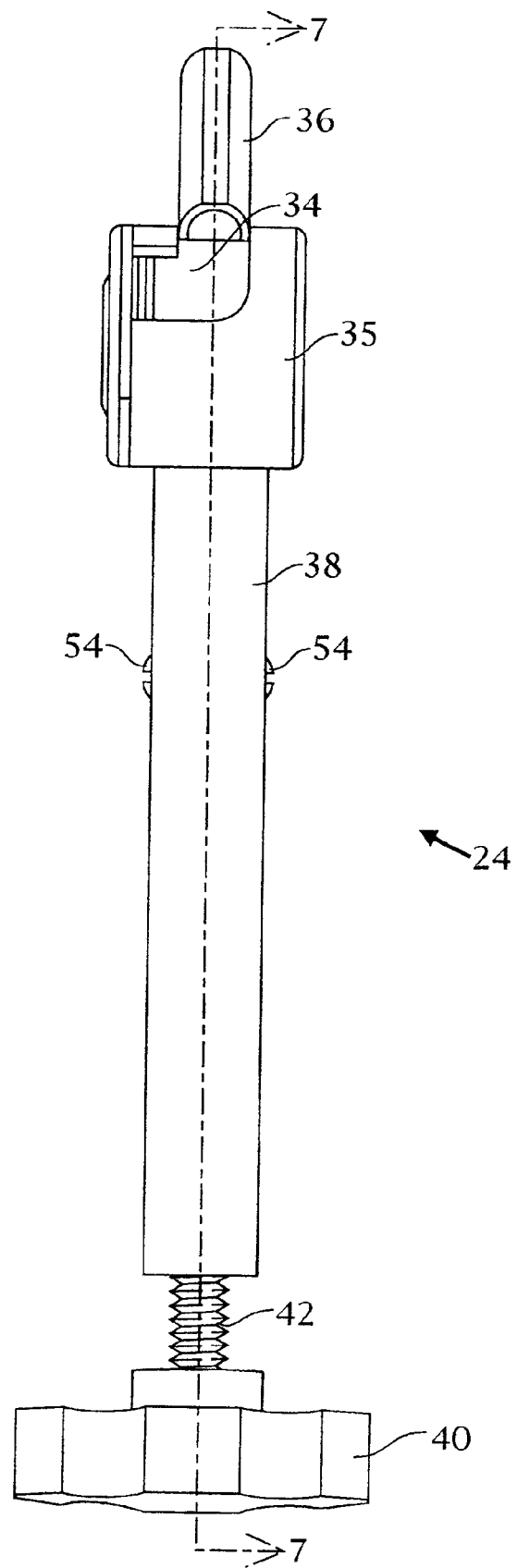
FIG. 6 is top plan view of the drive assembly for the carpal tunnel syndrome therapy device.
Figure 7:
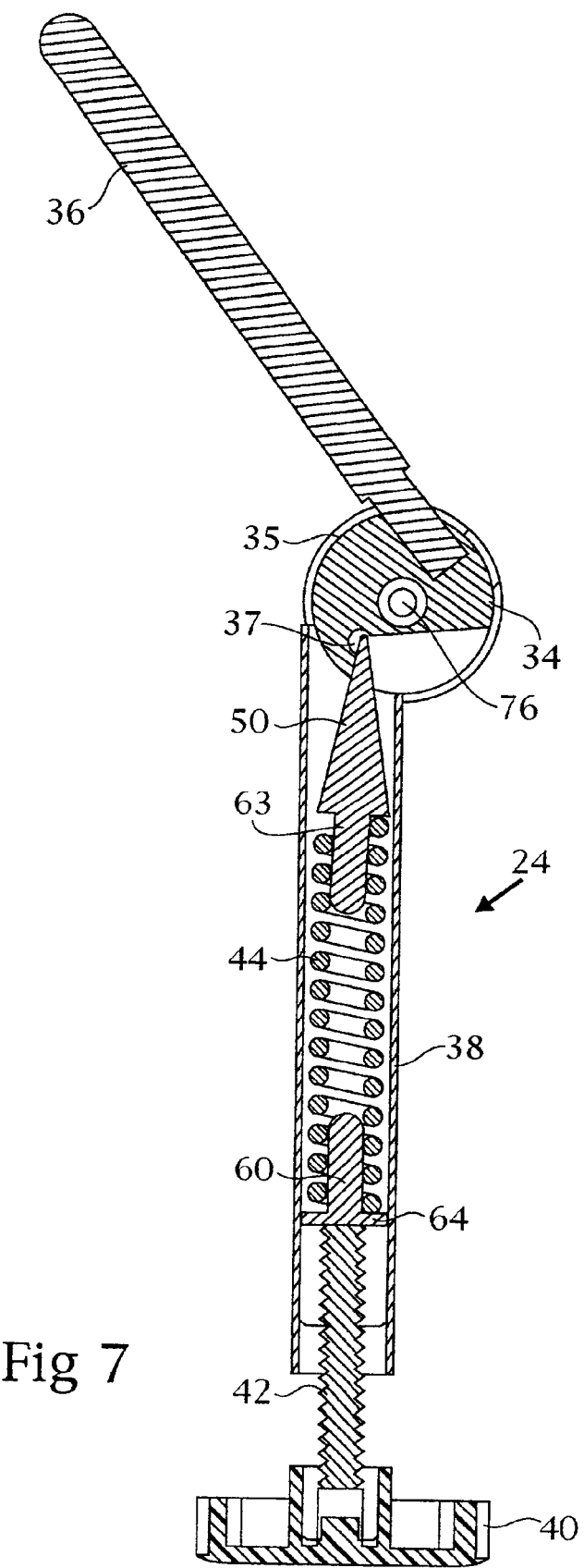
FIG. 7 is a cross-section thereof taken along 7—7 of FIG. 6.
Figure 10:
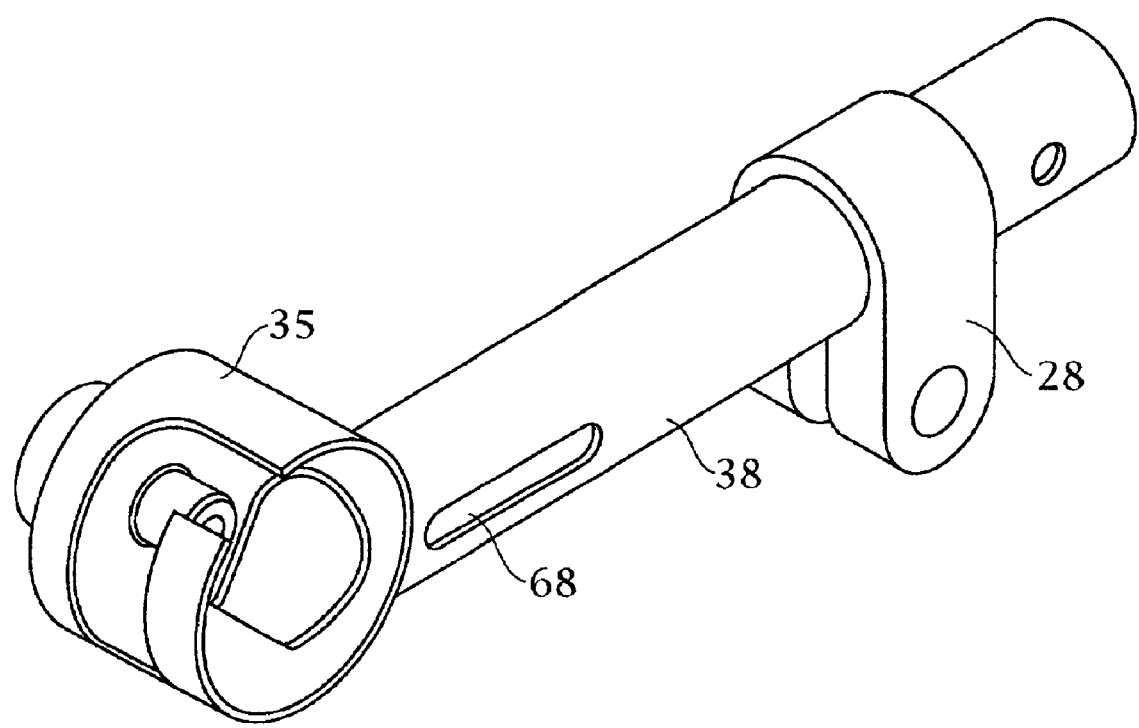
FIG. 10 is a perspective view of the housing head, tube and yoke sub-assembly of the therapy device.
Figure 11:
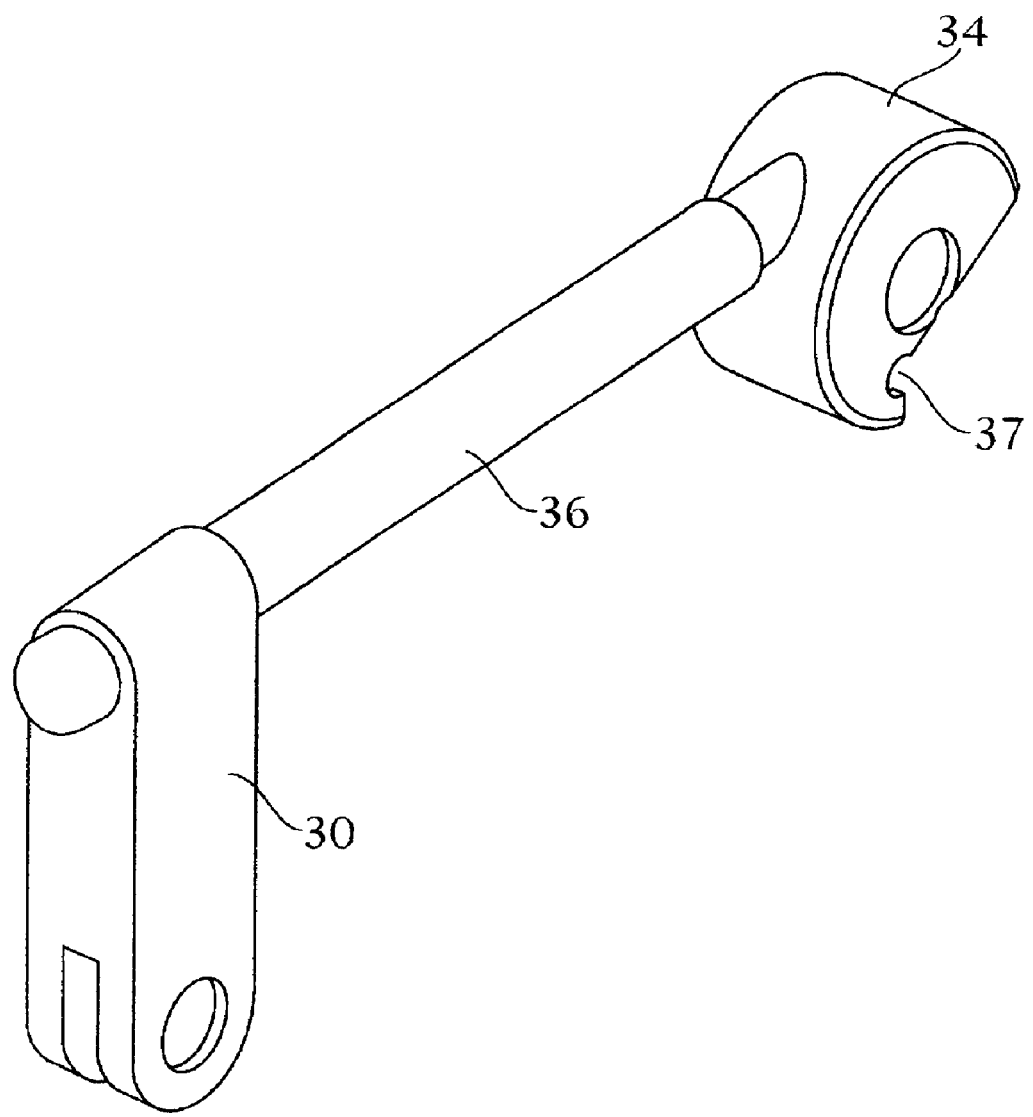
FIG. 11 is a perspective view of a stem rod yoke to rod and joint sub-assembly of the therapy device.
Figure 12:
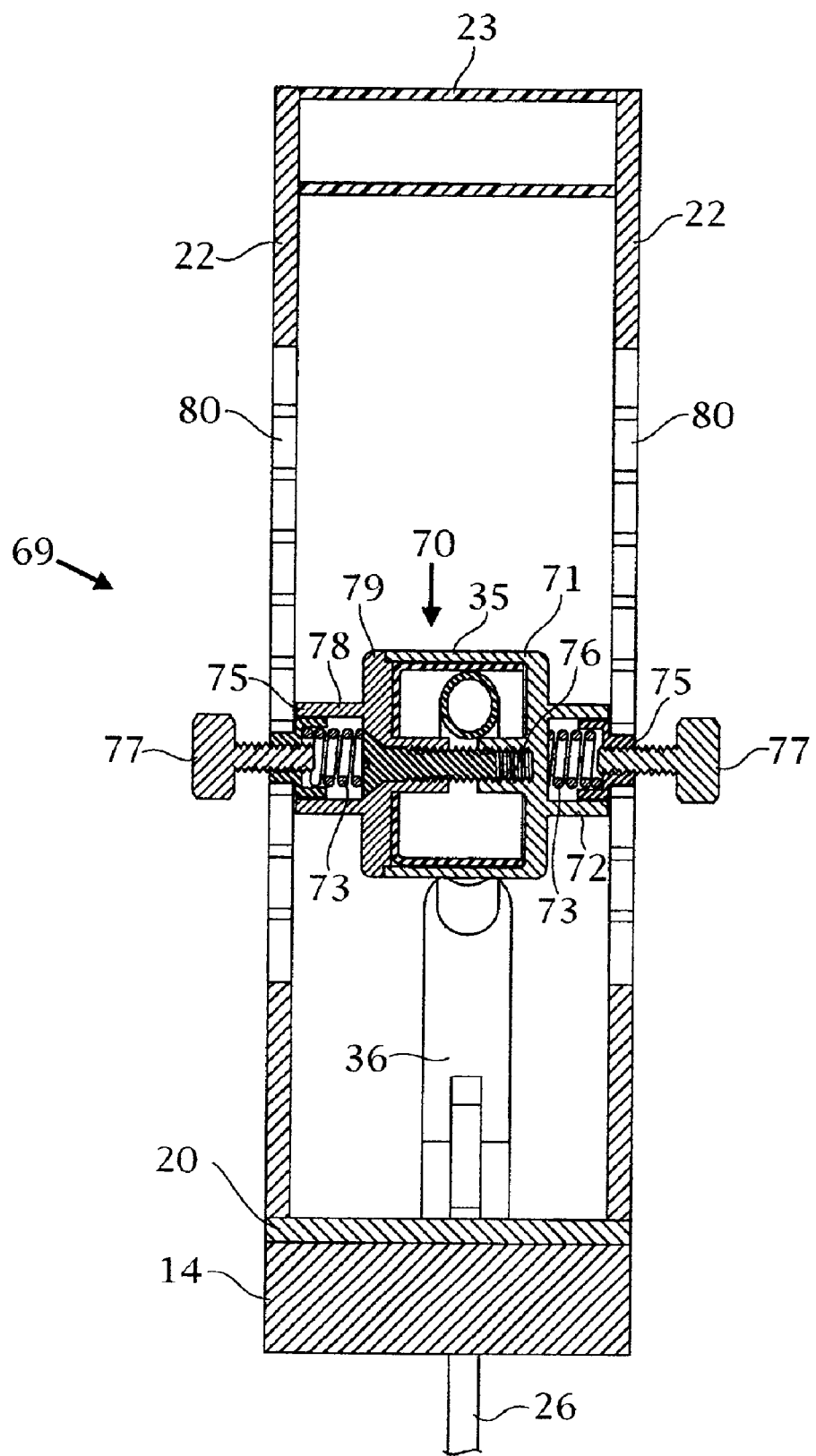
FIG. 12 is a sectional view of the counterforce taken along 12—12 of FIG. 2.

With special reference to FIGS. 6–7, there is shown a sectional view, taken along lines 7—7 of FIG. 6, of the drive assembly 24 contained in the housing tube 38, and main joint 34, housing tube head 35 with stem rod 36 attached to joint 34 which abuts chisel tip 50. Chisel tip 50 applies pressure to the joint 34 through compression spring 44 which in turn has pressure put on it through loading screw 42 and loading screw knob 40. As the loading screw knob 40 and loading screw 42 are tightened, more and more pressure can be applied to the compression spring 44 which in turn exerts more pressure on the stem rod 36. The force on stem rod 36 attached to stem rod yoke 30 produces a counter force on pad 14 to apply pressure to the top of the hand 41 shown in dashed lines in FIG. 1. The amount of pressure is indicated by indicator screw head 54 and indicator marker 56 (best shown in FIG. 4). Note that the scale is 0–9 with 9 indicating maximum pressure for that setting.

Figure 13:
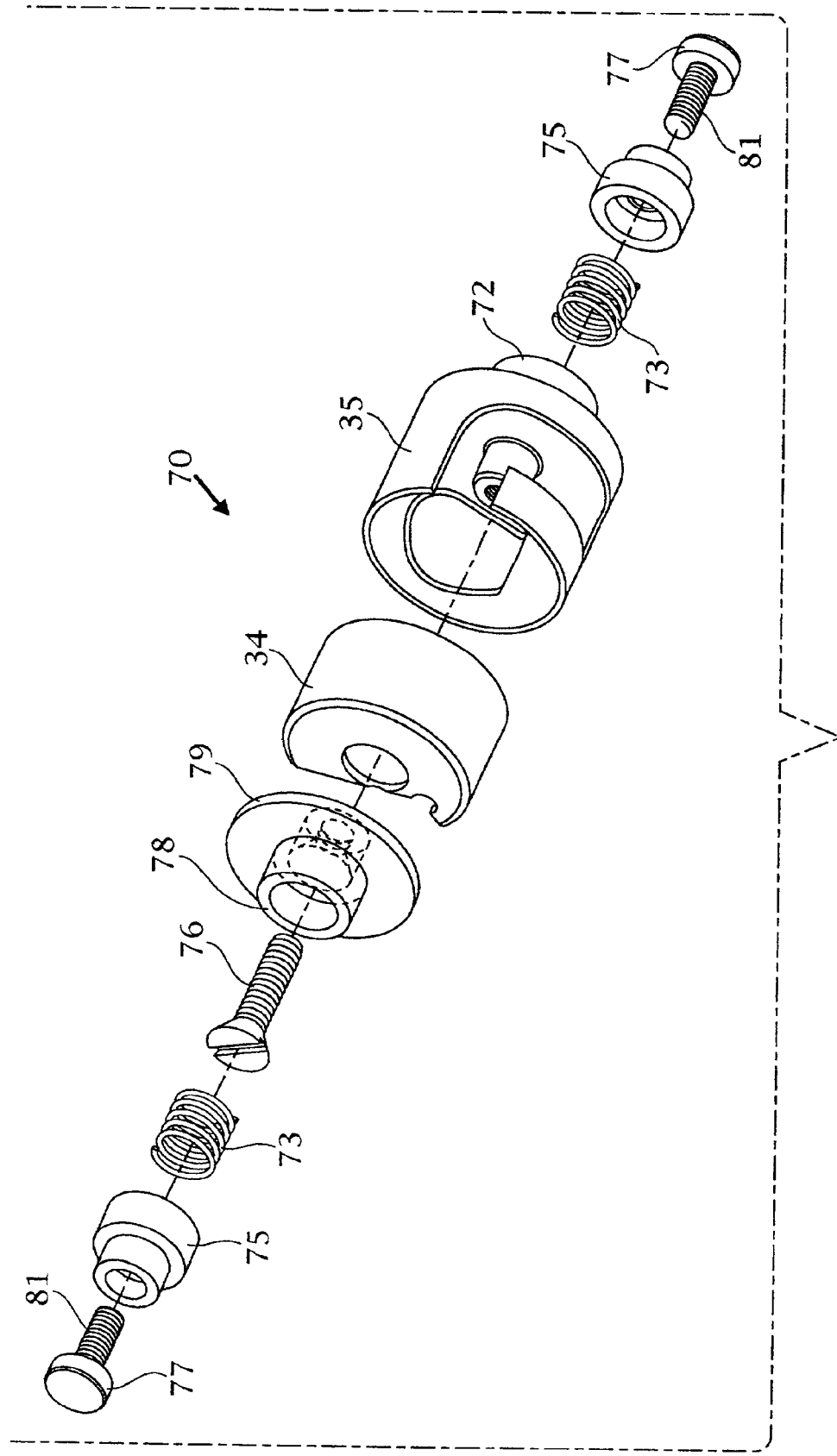
FIG. 13 is an exploded view showing the plunger release assembly.

In use the palm of the affected hand would be placed on pads 12. The counter force pad 14 would be placed over the top of the hand using the variable height sub-assembly 69 best shown in FIGS. 12 and 13. Once the counter force pad 14 is in place over the top of the hand, added pressure can be applied to the hand incrementally using loading screw knob 40. A more detailed method of use and protocol are set forth below.

With particular reference to FIGS. 8 and 9, an exploded view of the compression assembly 58 within the housing tube 38 is made up of two indicator bars 52 and a compression spring spacer 60, compression spring 44 and chisel tip unit 62 composed of a chisel tip 50 and boss 63. In operation the compression spring 44 is given tension by the loading screw 42 pressing against the bottom support 64 and the chisel tip 50 pressing against the main joint 34 in housing head 35. The indicator bar 52 rises as the loading screw 42 presses on the bottom support 64 of spring spacer 60 of the compression assembly 58. The compression mechanism is similar to that shown in U.S. Pat. No. 5,558,624.

Figure 4:
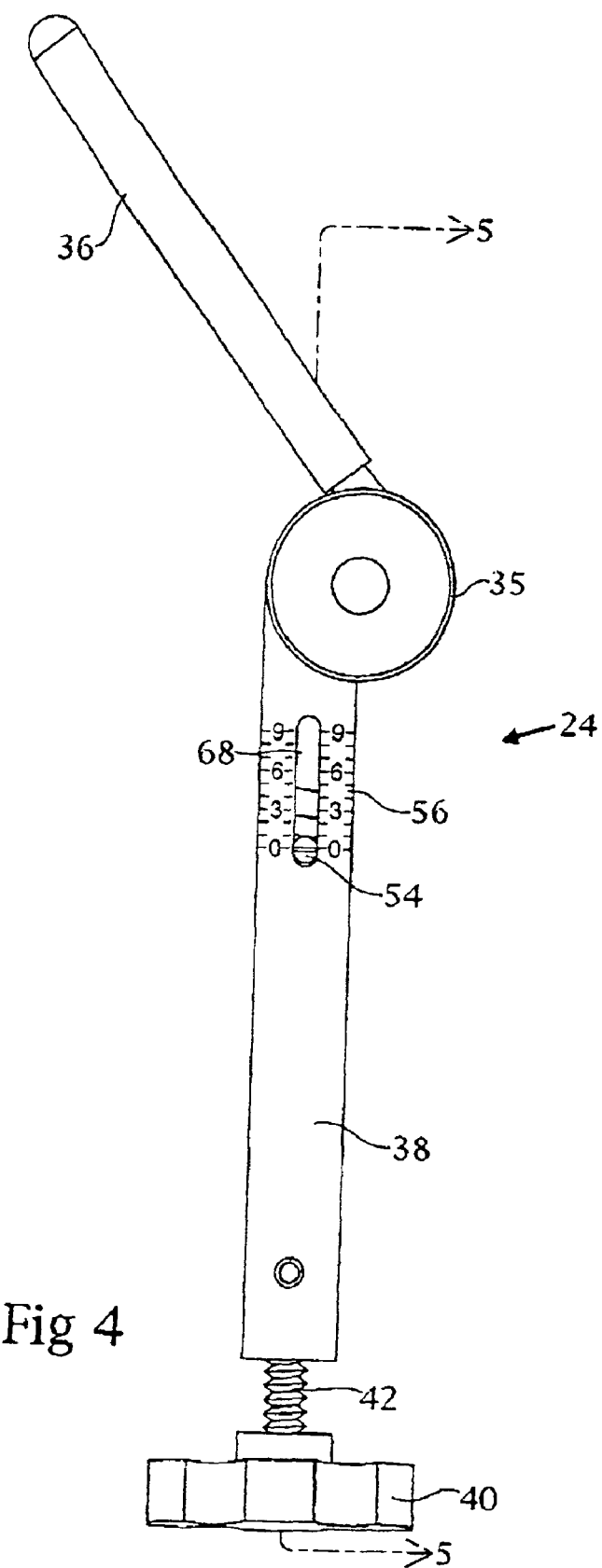
FIG. 4 is a front plan view of the drive assembly for the carpal tunnel syndrome therapy device.
Figure 5:
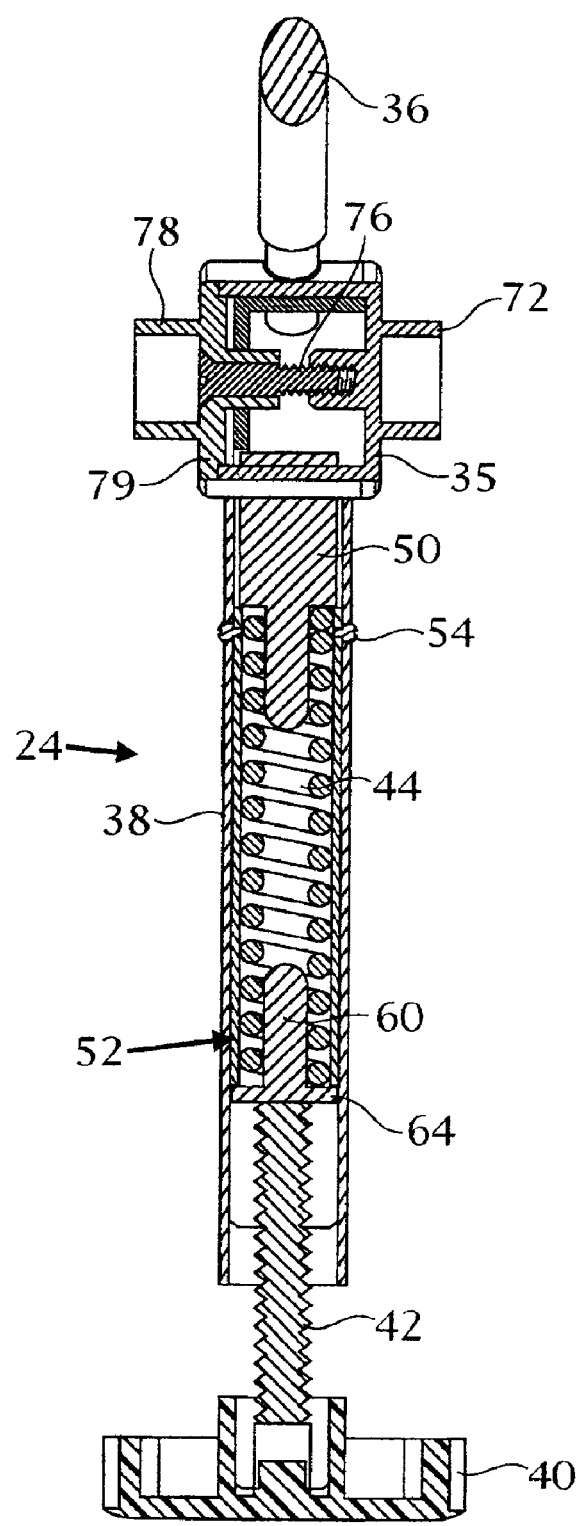
FIG. 5 is a cross-section taken along 5—5 of FIG. 4.

With special reference to FIGS. 1, 2 and 4, there is shown as part of the housing tube 38 a viewing slot 68 showing indicator screw 54. In FIG. 4, the viewing slot 68 is accompanied by a scale 56. The higher the number of the scale 56, the higher will be the compression or tension on the stem rod 36 and the greater the pressure on the hand during therapy.

With particular reference to FIGS. 12 through 30, various sub-assemblies of the carpal tunnel syndrome therapy device are described.

Counter Force Variable Height Adjustment Sub-assembly

With reference to FIGS. 1, 2, 12 and 13, there is provided a variable height adjustment sub-assembly 69 for the counter force 70 consisting principally of the head 35 for the housing tube 38 the head being integrally capped 71 on a first end with a collar 72 which receives a spring plunger spring 73 and over which is placed a tapped spring plunger 75 which in turn receives a threaded spring plunger button 77 into the tapped end of the spring plunger 75. The second end of the housing tube head 35 is provided with a removable plate cap 79 with collar 78 which receives a spring plunger spring 73, a spring plunger 75 and a spring plunger button 77. Housing tube head 35 and main joint 34 are joined and held in place by screw 76. In use the variable height adjustment sub-assembly is mounted between two counter force brackets 22 which are provided with a contiguous series of scalloped detent openings 80 to receive the spring plunger 75 of the counter force sub-assembly. Note that spring plungers 75 have a collar 74 and the housing head 35 has a collar 72 and the plate cap 79 has a collar 78 in which each of the spring plunger springs 73 are retained.

To adjust the height of the counter force sub-assembly 70, spring plunger buttons 77 on either side of the counter force sub-assembly are squeezed inward. This squeezing causes the spring plunger 75 and the spring plunger spring 73 to depress allowing narrower threaded portion 81 of spring plunger button 77 to line up with scalloped openings 80 allowing free movement up or down of counter force pad 14 held on counter force brackets 22. Once the proper height is attained, the spring plunger buttons 77 can be released and the spring plunger spring 73 expands to cause the spring plunger 75 to re-engage the scalloped openings 80 in the counter force brackets 22.

Foot Yoke Sub-assembly

With reference to FIGS. 1, 2 and 14–23, the pads 12 of the carpal tunnel syndrome therapy device 10 are attached to bracket 26 through foot yoke 18. There are two symmetrical foot yoke sub-assemblies 84. Each sub-assembly 84 is composed of a foot yoke 18, a foot yoke pivot pin 86, foot yoke torsion spring 88, a lateral adjustment screw 90 and lateral adjustment screw housing 91.

Figure 16:
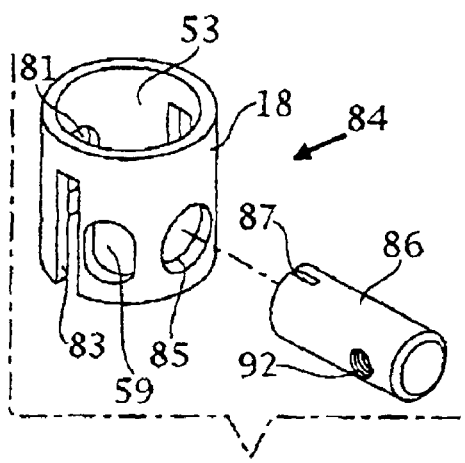
Figure 17:
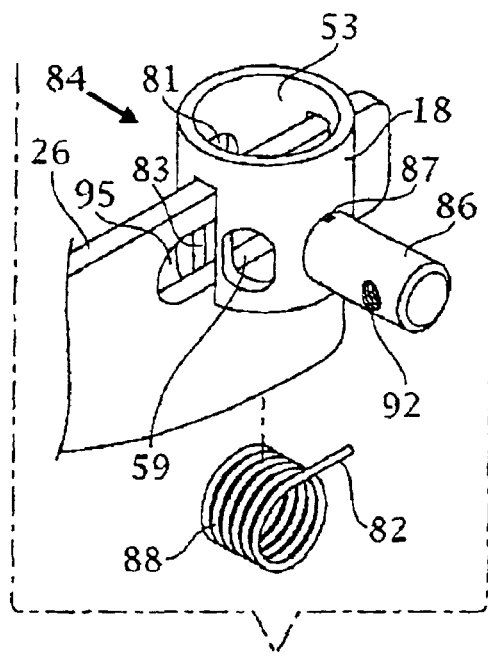
Figure 18:
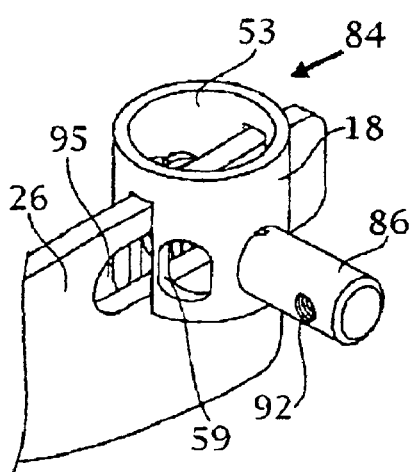
Figure 19:
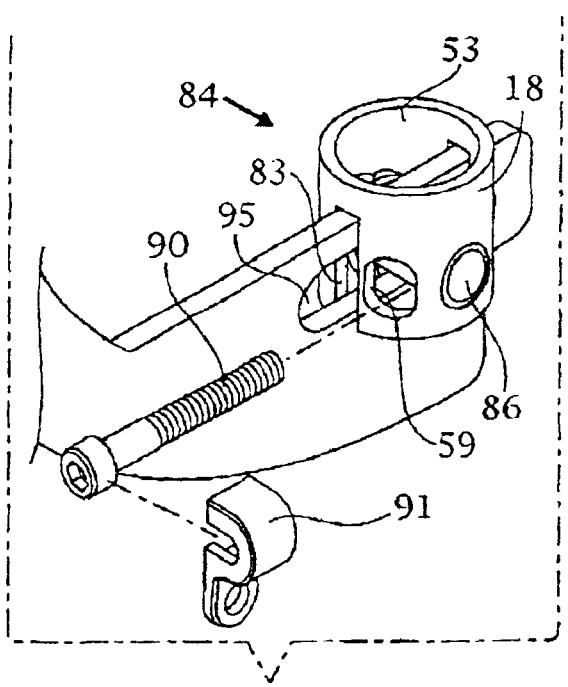
Figure 24:
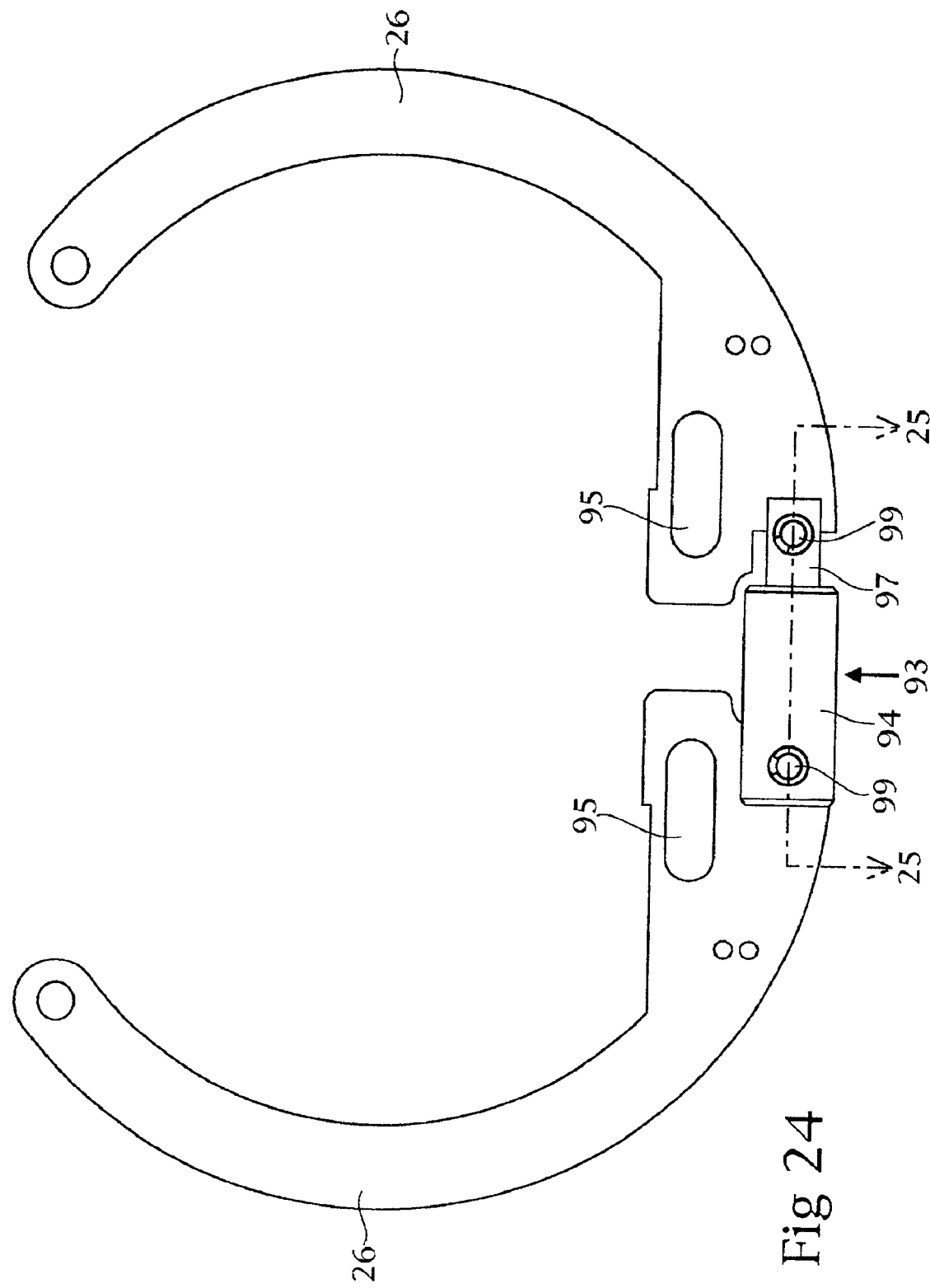
FIG. 24 is a front plan view of the spread connector attached to the brackets of the carpal tunnel therapy device.
Figure 25:
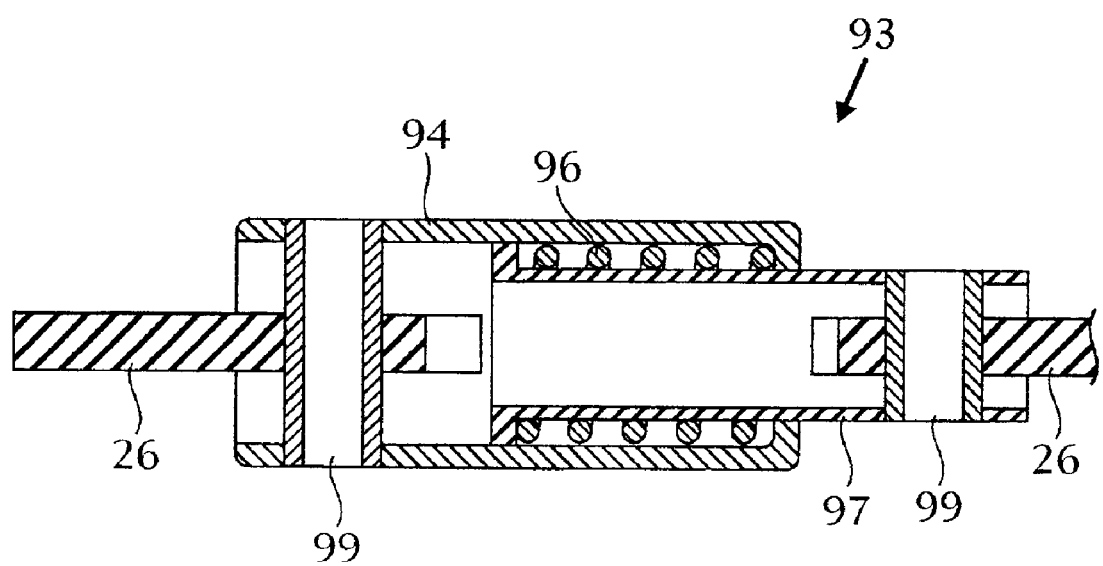
FIG. 25 is a sectional view thereof taken along 25—25 of FIG. 24.
Figure 26:
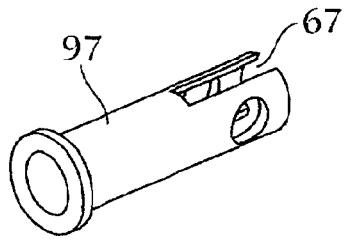
FIGS. 26–30 illustrate the components of the spread connector and the order for assembly of the spread connector.

To assemble the foot yoke sub-assembly 84 to bracket 26, foot yoke pin 86 is partially inserted into opening 85 of yoke as shown in FIGS. 16 and 17. Bracket 26 with opening 95 (best shown in FIG. 24) is inserted into slot 83 and pin 86 is further inserted through opening 95 of bracket 26. Spring 88 is then inserted into yoke 18 (FIG. 18) and slot 87 of pin 86 is lined up with diametric fold 89 of spring 88 as best shown in cross-sectional view of FIG. 15. Pin 86 is inserted further to protrude through opening 81 on the opposite side of yoke 18. As shown in FIGS. 19 and 20, lateral adjusting screw 90 is inserted through opening 59 into tapped hole 92 of the foot yoke pin 86. The tangential tail 82 of spring 88 buts against the inner wall 53 of the foot yoke 18 to provide spring tension to the foot yoke. Once the yoke 18 is on the bracket 26, the lateral adjusting screw housing can be attached with a fixed screw 98 or other securing means.

Adjusting lateral screw 90 provided in each yoke sub-assembly adjusts the pads 12 to accommodate the width of the palm of the hand.

Spring 88 serves to spring-load the yoke in an outward direction left and right, respectively and functions to counteract outward spreading that takes place when downward force is applied.

Spread Connector Sub-assembly

With reference to FIGS. 24–30, the carpal tunnel syndrome therapy device is provided with spread connector 93 attached to brackets 26 to adjust the spread of the brackets and accordingly the pair of yokes 18 and pads 12 attached thereto. The main components of the spread connector assembly 93 are the spread connector outer tube 94, spread connector spring 96 and spread connector inner tube 97.

Figure 29:
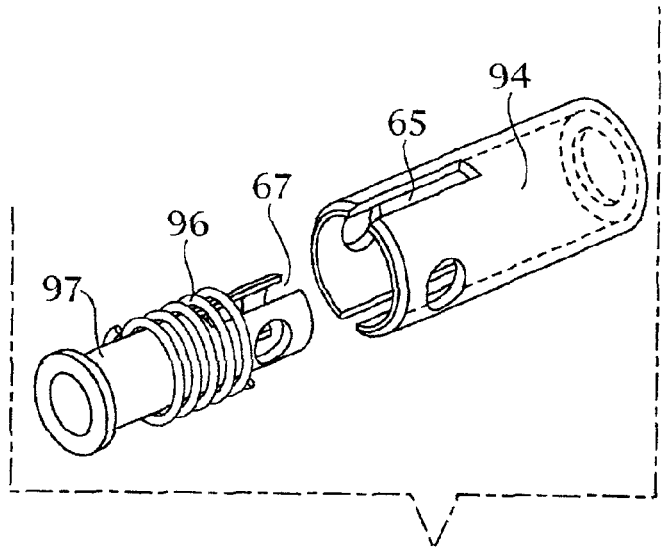
Figure 27:
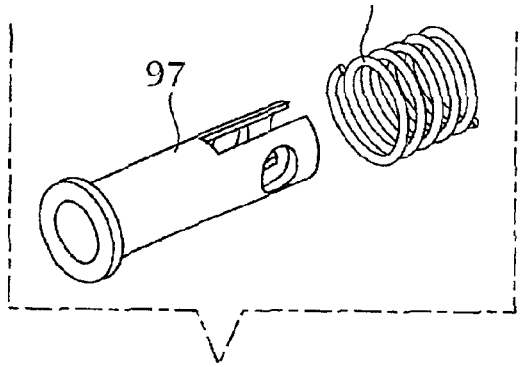
Figure 28:
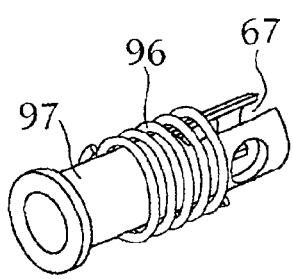
Figure 30:
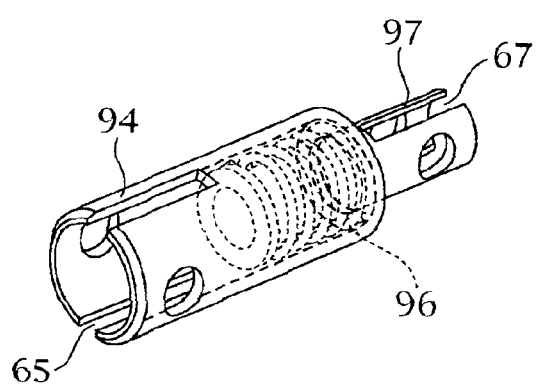

As shown in FIGS. 24–30, the spread connector assembly 93 is made by inserting spring 86 over inner tube 97 (FIGS. 26–28) and inserting both completely into outer tube 94 (FIGS. 29 and 30). The spread connector assembly is placed on bracket 26 through slots 65 and 67 and are held in place by a fixed screw 98, of course other fasteners known in the art could be used.

The spread connector serves to adjust the spread or spacing of the brackets 26 and to spread or close to accommodate the spread of the carpal pads 12. The spread connector also by virtue of the spring 96 holds the brackets inward and accordingly accomplishes presenting the carpal pads at the correct angularity at the initial fitting.

The stem rod 36 and housing tube 38 are attached to bracket 26 with stem rod yoke 30 held in place by a pivot pin 99. Pivot pins 99 are also employed to position the spread connector assembly 93 on brackets 26. While pivot pins have been used herein, other holding means such as rivets or bolts could be used.

Figure 31A:
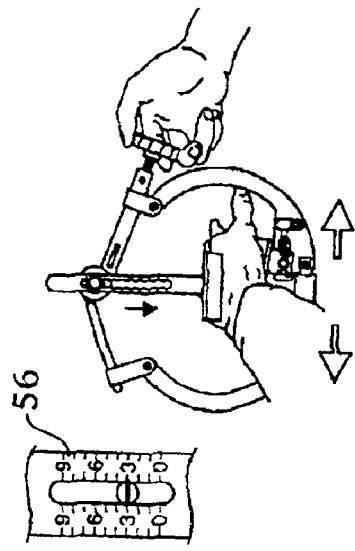
FIGS. 31A–31E are a sequence for using the carpal tunnel therapy device.
Figure 31B:
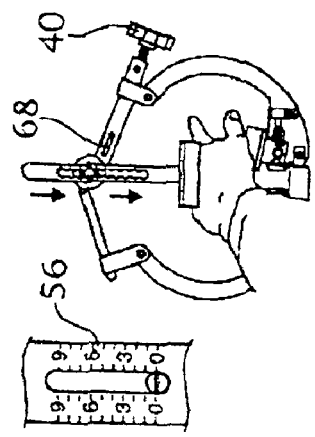
Figure 31C:
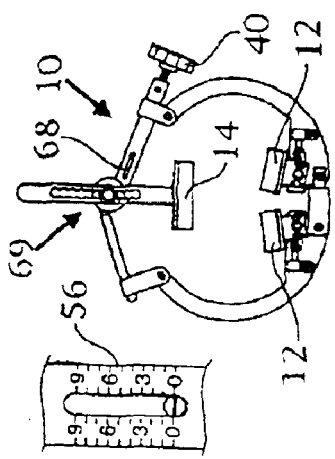
Figure 31D:
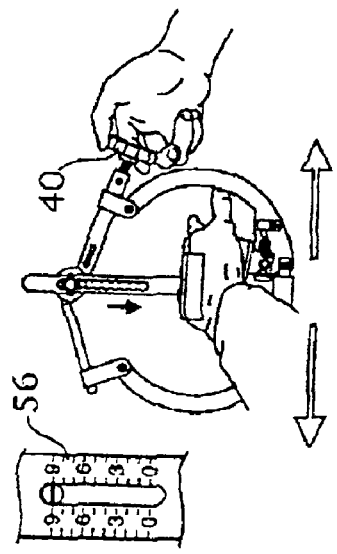
Figure 31E:
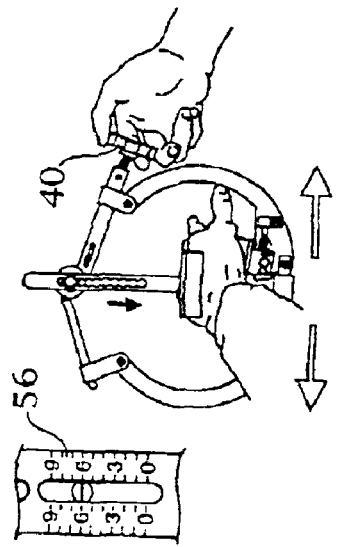

With reference to FIGS. 31A–31E, there is shown the use of the carpal tunnel syndrome therapy device. As noted, at the start of therapy, the scale 56 is set at zero. The palm of the hand is placed on carpal pads 12 and the counter force pads 14 are placed over the top of the hand by using the variable height adjusting mechanism 69 (described in FIGS. 12–13). Once the hand is set between the carpal pad 12 and counter force pad 14, pressure can be applied by using loading screw knob 40 (FIGS. 31B and 31C). On an on-going basis pressure is increased using loading screw knob 40 and the amount of pressure can be viewed in scale 56. The amount of pressure indicated is graduated as see scale of 0–9, with 9 being the greater pressure. This pressure action is designed to further spread the carpal tunnel area.

The carpal tunnel therapy device is primarily intended to be a passive therapy device in that it is to be worn for extended periods of time to thereby relieve carpal tunnel area and thereby prevent invasive surgery.

In FIGS. 31A–31E, the vertical arrows show the height adjustment for the counter force pads 14 and the horizontal arrows show the direction of spread of the spread connector.

The therapy device of this invention is designed to be used 1–3 times a day for 30–60 minutes in each session. The treatment programs begin with lower pressure or tension on the device and progressing to higher pressure as tolerated to relieve the pain, stress, numbness brought about by the carpal tunnel syndrome.

Obviously, many modifications may be made without departing from the basic spirit of the present invention. Accordingly, it will be appreciated by those skilled in the art that within the scope of the appended claims, the invention may be practiced other than has been specifically described herein.

What is claimed is:

1. A therapeutic device to be used to treat carpal tunnel syndrome comprising a pair of brackets having mounted thereon and movable relative to said brackets and is a pair of spring loaded carpal foot yokes having mounted thereon a pair of carpal pads spreadable relative to each other for receiving the palm of the hand in combination with a graded compression means positioned over said pair of carpal pads such that said compression means is movable relative to said brackets and is able to be applied in a graded fashion to the band to relieve the effect of carpal tunnel syndrome.

2. A therapeutic device to be used to treat carpal tunnel syndrome comprising a means for receiving the palm of the hand in combination with a graded counter force compression means positioned over the means for receiving the palm of the hand and wherein the means for receiving the palm of the hand are a pair of brackets having mounted thereon and movable relative to said brackets a pair of spring loaded carpal foot yokes having mounted thereon a pair of carpal pads which can be spread apart relative to each other and are flexibly placed relative to the counter force compression means such that the graded counter force compression means is movable relative to said brackets and when applied to the hand will spread the palm of the hand and remedy the effect of the carpal tunnel syndrome.

3. The therapeutic device for relieving carpal tunnel syndrome of claim 2 further comprising said pair of carpal pads for receiving the palm of the hand and a counter force pad to be applied to the top of the hand wherein the counter force pad is attached to a means for adjusting height to snugly place the counter force pad over the top of the hand and a means for applying graded pressure to the hand thereby relieving the effects of carpal tunnel syndrome.

4. The device of claim 3 wherein the carpal pads and counter force pad are all supported by a pair of brackets.

5. A therapeutic device to be used to treat carpal tunnel syndrome comprising, 1) a pair of brackets having mounted thereon and movable relative to said brackets a pair of spring loaded carpal foot yokes having mounted thereon a pair of carpal pads spreadable relative to each other for receiving the palm of the hand and being flexibly positioned under a means disposed to contact the top of the hand for applying pressure to the hand, 2) the means for applying pressure to the top of the hand being attached to a vertical adjusting means and movable relative to said brackets, and 3) the vertical adjusting means retaining thereon a means creating pressure to apply to the hand.

6. The therapeutic device of claim 5 wherein the means for applying pressure to the hand comprises a chisel tip applying pressure to a main joint.

7. The therapeutic device of claim 6 wherein the means for applying pressure to the hand has a means for graduating the pressure.

8. The therapeutic device of claim 5 wherein the carpal foot yokes and the carpal pads supported thereon can be laterally displaced by using a spread connector to which the yokes are attached.

9. A method for treating carpal tunnel syndrome comprising, 1) placing the palm of the hand onto a pair of carpal pads spreadable relative to each other supported on a pair of yokes, movably mounted to a pair of brackets, 2) lowering a counter force pad attached and movable relative to a counter force bracket and compression assembly having a means for graduating the pressure on the counter force pad onto the top of the hand and 3) applying graduated pressure to the palm of the hand thereby spreading the palm of the hand to relieve carpal tunnel syndrome.

* * * * *

UNITED STATES PATENT AND TRADEMARK OFFICE
CERTIFICATE OF CORRECTION

PATENT NO.    : 6,908,475 B2
DATED         : June 21, 2005
INVENTOR(S)   : Hepburn et al.

It is certified that error appears in the above-identified patent and that said Letters Patent is hereby corrected as shown below:

Column 7,
Line 16, cancel the word "and" second occurrence.
Line 23, the word "band" should be changed to -- hand --.

Signed and Sealed this

Eighteenth Day of October, 2005

JON W. DUDAS
*Director of the United States Patent and Trademark Office*